United States Patent
Liu et al.

(10) Patent No.: US 11,653,885 B2
(45) Date of Patent: May 23, 2023

(54) SYSTEM AND METHOD FOR MEDICAL IMAGING AND DIAGNOSIS

(71) Applicant: SHANGHAI UNITED IMAGING HEALTHCARE CO., LTD., Shanghai (CN)

(72) Inventors: Weiping Liu, Shanghai (CN); Shitao Liu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 1612 days.

(21) Appl. No.: 15/791,524

(22) Filed: Oct. 24, 2017

(65) Prior Publication Data

US 2018/0110487 A1    Apr. 26, 2018

Related U.S. Application Data

(63) Continuation of application No. PCT/CN2017/099770, filed on Aug. 30, 2017.

(30) Foreign Application Priority Data

Oct. 25, 2016 (CN) .......................... 201610932561.4

(51) Int. Cl.
*A61B 6/04* (2006.01)
*A61N 5/10* (2006.01)
(Continued)

(52) U.S. Cl.
CPC .......... *A61B 6/0471* (2013.01); *A61B 6/0487* (2020.08); *A61N 5/1069* (2013.01);
(Continued)

(58) Field of Classification Search
CPC ....... A61B 6/04; A61B 6/0407; A61B 6/0471; A61B 6/0487; A61B 5/055; A61B 6/032; A61N 5/1069
(Continued)

(56) References Cited

U.S. PATENT DOCUMENTS 3,588,500 A * 6/1971 Koerner .................... A61B 6/10
5/601
3,612,509 A * 10/1971 Boston ................. A61G 7/1098
269/98

(Continued)

FOREIGN PATENT DOCUMENTS

| CN | 202161329 U | 3/2012 |
|----|-------------|--------|
| CN | 105877772 A | 8/2016 |

(Continued)

OTHER PUBLICATIONS

International Search Report in PCT/CN2017/099770 dated Nov. 30, 2017, 5 pages.
(Continued)

*Primary Examiner* — Robert G Santos
(74) *Attorney, Agent, or Firm* — Metis IP LLC

(57) ABSTRACT

A device for transferring a subject in a medical procedure may be provided. The device may include a transmission assembly configured to transfer a subject to a scanning region of a medical device. The device may further include a supporting assembly supporting the transmission assembly. The supporting assembly may include at least one board and at least two supporting units supporting the at least one board. The at least two supporting units may be disposed at two sides of the scanning region of the medical device.

19 Claims, 9 Drawing Sheets

(51) Int. Cl.
*A61B 6/03* (2006.01)
*A61B 5/055* (2006.01)
*A61G 13/00* (2006.01)

(52) U.S. Cl.
CPC .............. *A61B 5/055* (2013.01); *A61B 6/032* (2013.01); *A61B 6/037* (2013.01); *A61B 6/0407* (2013.01); *A61B 6/0442* (2013.01); *A61G 13/00* (2013.01)

(58) Field of Classification Search
USPC ............... 5/601, 600, 943; 378/209, 208, 20
See application file for complete search history.

(56) References Cited

U.S. PATENT DOCUMENTS

| | | | |
|---|---|---|---|
| 4,131,802 A | 12/1978 | Braden et al. | |
| 4,773,637 A * | 9/1988 | Jarin | A61B 6/0487 5/601 |
| 5,210,893 A * | 5/1993 | Uosaki | A61B 5/055 5/601 |
| 5,864,901 A * | 2/1999 | Blumel | A61G 7/0573 5/610 |
| 6,363,555 B1 * | 4/2002 | LaRose | A61G 7/1098 5/81.1 R |
| 6,499,156 B1 * | 12/2002 | Dirst | A61G 7/1019 5/81.1 C |
| 6,621,093 B2 * | 9/2003 | Tajima | A61B 6/4216 378/189 |
| 6,668,403 B2 * | 12/2003 | Seufert | A61B 6/0471 5/601 |
| 7,437,785 B2 * | 10/2008 | Farooqui | A61B 6/0487 5/601 |
| 7,634,827 B2 * | 12/2009 | Gagneur | A61B 5/704 5/601 |
| 7,810,186 B2 * | 10/2010 | Doleschal | A61B 6/0487 5/601 |
| 8,621,689 B2 * | 1/2014 | Dong | A61B 5/055 5/601 |
| 8,931,125 B2 * | 1/2015 | Fang | A61B 5/055 5/601 |
| 9,549,706 B2 * | 1/2017 | Zhang | A61B 6/0471 |
| 10,130,315 B2 * | 11/2018 | Hou | A61B 6/0471 |
| 10,863,956 B2 * | 12/2020 | Zilberstien | A61B 6/04 |
| 11,246,544 B2 * | 2/2022 | Hou | A61B 5/055 |
| 11,457,884 B2 * | 10/2022 | Zilberstien | A61B 6/04 |
| 2001/0019113 A1 * | 9/2001 | Tajima | G03B 42/02 378/189 |
| 2002/0112288 A1 | 8/2002 | Seufert | |
| 2005/0204472 A1 * | 9/2005 | Gagneur | A61B 5/704 5/601 |
| 2007/0226906 A1 * | 10/2007 | Farooqui | A61B 6/0487 5/601 |
| 2008/0060133 A1 * | 3/2008 | Farooqui | A61B 6/0487 5/601 |
| 2008/0098526 A1 * | 5/2008 | Doleschal | A61B 6/0487 5/616 |
| 2010/0040197 A1 | 2/2010 | Maniawski et al. | |
| 2012/0000016 A1 * | 1/2012 | Dong | A61B 5/055 5/601 |
| 2013/0081489 A1 * | 4/2013 | Fang | A61B 6/0471 74/89.34 |
| 2014/0051964 A1 | 2/2014 | Hori | |
| 2014/0208509 A1 * | 7/2014 | Zhang | A61B 6/0471 5/601 |
| 2017/0164912 A1 * | 6/2017 | Hou | A61B 6/0471 |
| 2018/0110487 A1 * | 4/2018 | Liu | A61N 5/1069 |
| 2019/0282187 A1 * | 9/2019 | Hou | A61B 6/0407 |
| 2020/0297296 A1 * | 9/2020 | Zilberstien | G01T 7/00 |
| 2021/0093270 A1 * | 4/2021 | Zilberstien | G01T 7/00 |

FOREIGN PATENT DOCUMENTS

| | | |
|---|---|---|
| CN | 106419943 A | 2/2017 |
| JP | H05317306 A | 12/1993 |
| JP | H0956711 A | 3/1997 |
| WO | 2018076924 A1 | 5/2018 |

OTHER PUBLICATIONS

Written Opinion in PCT/CN2017/099770 dated Nov. 30, 2017, 5 pages.

* cited by examiner

100

400

SYSTEM AND METHOD FOR MEDICAL IMAGING AND DIAGNOSIS

CROSS-REFERENCE TO RELATED APPLICATIONS

This application is a continuation of International Application No. PCT/CN2017/099770 filed on Aug. 30, 2017, which claims priority to Chinese Patent Application No. 201610932561.4 filed on Oct. 25, 2016, the entire contents of which are hereby incorporated by reference.

TECHNICAL FIELD

The present disclosure generally relates to medical system, and more particularly, a system and method for medical imaging and diagnosis.

BACKGROUND

Various imaging techniques have been widely used in medical diagnosis, radiation therapy planning, surgery planning and other medical procedures, such as an X-ray photography, a magnetic resonance imaging (MRI), a computed tomography (CT), a positron emission tomography (PET), etc.

Generally, a couch may be used to support and/or transfer a subject to be examined to a scanning region of an imaging device. It is important to keep the couch in the same horizontal direction during a medical procedure. For example, for a multi-modality imaging procedure (e.g., a PET-CT), as the multi-modality imaging device may share one single couch to generate one or more images, any variations of the couch position during imaging may cause inaccurate imaging result. Furthermore, a multi-modality image (e.g., a PET/CT image) may be reconstructed based on an image fusion technique by fusing, for example, a CT image and a PET image relating to the same anatomical plane. Thus, the couch needs to stay in the same horizontal direction during a multi-modality imaging procedure. However, a couch loaded with a subject (e.g., a patient) may sag or deflect when the couch moves along the longitudinal direction of the couch to a scanning region of an imaging device, such as a CT scanner, a PET scanner, a multi-modality scanner, etc. As a result, the quality of the fused image may be poor due to the variations of the couch position. Thus, it is desirable to provide systems for improving a sag or bend of a couch for supporting a subject in an imaging procedure.

SUMMARY

According to an aspect of the present disclosure, a device for transferring a subject in a medical procedure is provided. The device may include a transmission assembly configured to transfer a subject to a scanning region of a medical device and a supporting assembly supporting the transmission assembly. The supporting assembly may include at least one board and at least two supporting units supporting the at least one board. The at least two supporting units may be disposed at two sides of the scanning region of the medical device.

In some embodiments, the transmission assembly may include at least one transmission belt and at least one driving component configured to drive the at least one transmission belt.

In some embodiments, one of the at least two supporting units may be connected to a gantry of the medical device.

In some embodiments, the at least one driving component may further include a first rotation wheel and a second rotation wheel. In some embodiments, the at least one transmission belt may be configured to encompass the first rotation wheel, the second rotation wheel and the at least one board, and the first rotation wheel and the second rotation wheel may be configured to rotate to drive a rotation of the at least one transmission belt.

In some embodiments, each of the first rotation wheel and the second rotation wheel may be configured with a gear, respectively.

In some embodiments, the transmission belt may be configured with a plurality of teeth being coupled with the gear, and the at least one board is configured with a groove to accommodate the plurality of teeth.

In some embodiments, the at least one driving component may further include a first winding component and a second winding component. The first winding component and the second winding component may be connected to two ends of the at least one transmission belt, respectively.

In some embodiments, the transmission assembly may further include at least one first adjustment component configured to adjust a tension force of the at least one transmission belt.

In some embodiments, the at least one first adjustment component may include at least one third rotation wheel, the at least one transmission belt encompassing the at least one third rotation wheel.

In some embodiments, the at least one third rotation wheel may be configured to be a driving wheel to drive the at least one transmission belt to move.

In some embodiments, the transmission assembly may further include at least one second adjustment component configured to adjust a space between the at least one board and the at least one transmission belt, the at least one second adjustment component being connected to the supporting assembly.

In some embodiments, the supporting assembly may further include at least one third adjustment component connected to at least one of the at least two supporting units, the at least one third adjustment component being configured to adjust a height of the at least one board.

In some embodiments, the at least one third adjustment component may include a first adjustment unit and a second adjustment unit. The first adjustment unit and the second adjustment may be connected to the at least two supporting unit, respectively.

In some embodiments, the at least one third adjustment component may be driven by at least one of a hydraulic cylinder or a motor.

In some embodiments, the supporting assembly may include a plurality of boards, and each of the plurality of boards may include at least two supporting units supporting the each of the plurality of boards.

According to an aspect of the present disclosure, a system for performing a medical procedure is provided. The system may include a medical device including a scanning region being configured to accommodate a subject and a device configured to transfer the subject to the scanning region. The device may include a transmission assembly configured to transfer a subject to a scanning region of a medical device and a supporting assembly supporting the transmission assembly. The supporting assembly may include at least one board and at least two supporting units supporting the at least one board. The at least two supporting units may be disposed at two sides of the scanning region of the medical device.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
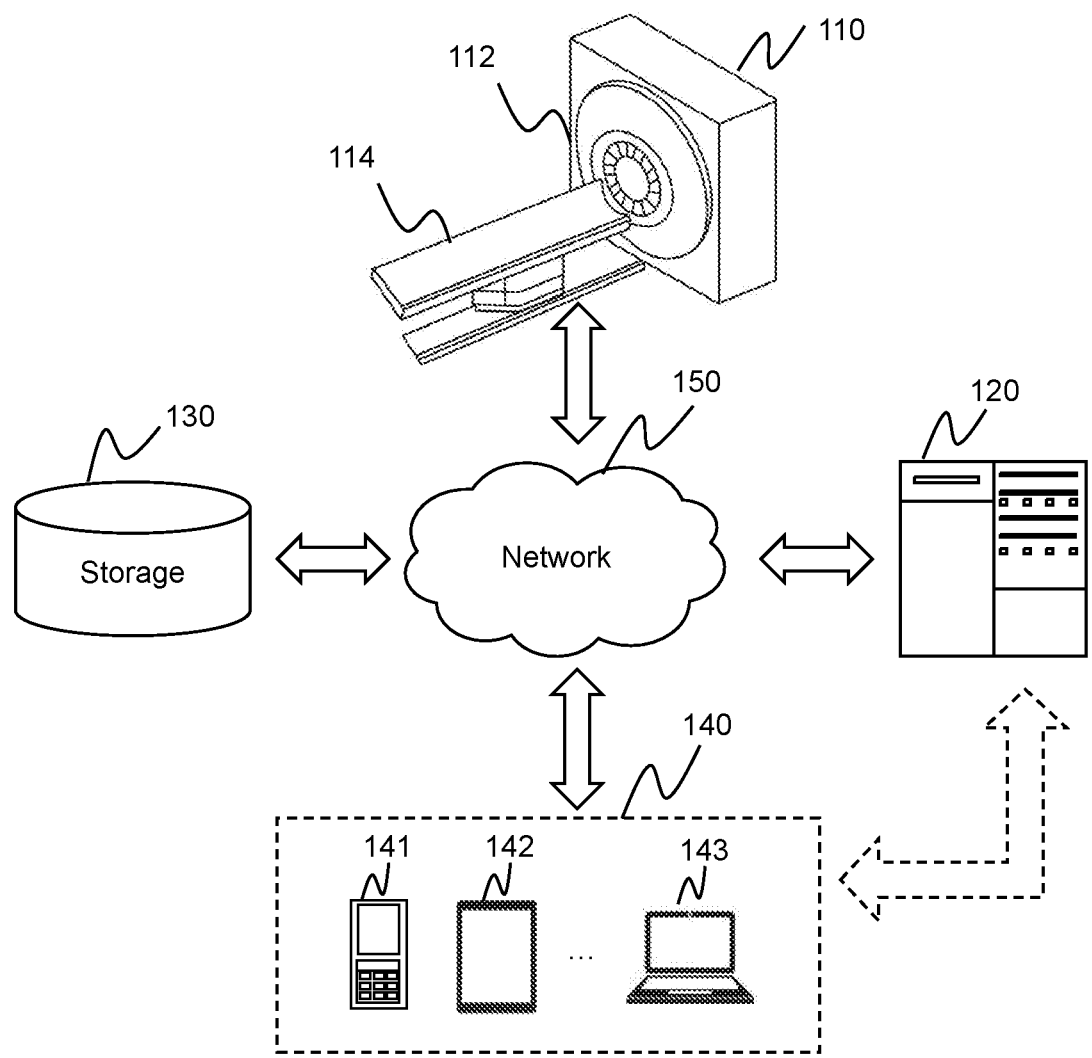
FIG. 1 is a schematic diagram illustrating an exemplary imaging system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by other expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. It will be further appreciated that hardware modules/units/blocks may be included in connected logic components, such as gates and flip-flops, and/or can be included of programmable units, such as programmable gate arrays or processors.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

For illustration purposes, the following description is provided to help better understanding an imaging process. It is understood that this is not intended to limit the scope of the present disclosure. For persons having ordinary skills in the art, a certain amount of variations, changes and/or modifications may be deducted under guidance of the present disclosure. Those variations, changes and/or modifications do not depart from the scope of the present disclosure.

Provided herein are systems and components for medical imaging or medical treatment. In some embodiments, the medical system may include an imaging system. The imaging system may include a single modality imaging system and/or a multi-modality imaging system. The single modality imaging system may include, for example, an X-ray imaging system, a computed tomography (CT) system, a magnetic resonance imaging (MRI) system, an ultrasonography system, a positron emission tomography (PET) system, or the like, or any combination thereof. The multi-modality imaging system may include, for example, a positron emission tomography-magnetic resonance imaging (PET-MRI) system, a positron emission tomography-computed tomography system (PET-CT) system, a single photon emission computed tomography-magnetic resonance imaging (SPECT-MRI) system, a digital subtraction angiography-magnetic resonance imaging (DSA-MRI) system, etc. In some embodiments, the medical system may include a treatment system. The treatment system may include a treatment plan system (TPS), an image-guide radiotherapy (IGRT), etc. Merely by way of example, the treatment system may include an CT guided radiotherapy system.

An aspect of the present disclosure relates to systems and methods for medical imaging and diagnosis. In some embodiments, a couch may be used to transfer a subject to a scanning region of a medical device in a medical procedure. In some embodiments, the couch may include a supporting assembly and a transmission assembly connected to the supporting assembly. The supporting assembly may include one or more boards and at least two supporting units configured to support each of the one or more boards. The transmission assembly may include a transmission belt and a driven component. The transmission belt may be driven by the driven component to transfer a subject to a scanning region of a medical device. The present disclosure employs at least two supporting units to stabilize the couch during the transferring of the subject to the scanning region of a medical device. Therefore, the image fusion quality of the multi-modality imaging may be improved.

For illustration purposes, the disclosure describes systems and methods for imaging system. It should be noted that the imaging system 100 described below is merely provided for illustration purposes, and not intended to limit the scope of the present disclosure.

FIG. 1 is a schematic diagram illustrating an exemplary imaging system 100 according to some embodiments of the present disclosure. As shown, the imaging system 100 may include a scanner 110, a processing engine 120, a storage 130, one or more terminal(s) 140, and a network 150. In some embodiments, the scanner 110, the processing engine 120, the storage 130, and/or the terminal(s) 140 may be connected to and/or communicate with each other via a wireless connection (e.g., the network 150), a wired connection, or a combination thereof. The connection between the components in the imaging system 100 may be variable. Merely by way of example, the scanner 110 may be connected to the processing engine 120 through the network 150, as illustrated in FIG. 1. As another example, the scanner 110 may be connected to the processing engine 120 directly. As a further example, the storage 130 may be connected to the processing engine 120 through the network 150, as illustrated in FIG. 1, or connected to the processing engine 120 directly. As still a further example, the terminal(s) 140 may be connected to the processing engine 120 through the network 150, as illustrated in FIG. 1, or connected to the processing engine 120 directly.

The scanner 110 may generate or provide image data via scanning a subject, or a part of the subject. The scanner 110 may include a single-modality scanner and/or multi-modality scanner. The single-modality may include, for example, a computed tomography (CT) scanner, a positron emission tomography (PET) scanner, a magnetic resonance imaging (MRI) scanner, etc. The multi-modality scanner may include a single photon emission computed tomography-computed tomography (SPECT-CT) scanner, a positron emission tomography-computed tomography (PET-CT) scanner, a computed tomography-ultra-sonic (CT-US) scanner, a magnetic resonance imaging-computed tomography (MRI-CT) scanner, or the like, or a combination thereof. In some embodiments, the subject may include a body, a substance, an object, or the like, or a combination thereof. In some embodiments, the subject may include a specific part of a body, such as a head, a thorax, an abdomen, or the like, or a combination thereof. In some embodiments, the subject may include a specific organ or region of interest, such as an esophagus, a trachea, a bronchus, a stomach, a gallbladder, a small intestine, a colon, a bladder, a ureter, a uterus, a fallopian tube, etc.

In some embodiments, the scanner 110 may include a gantry 112 and a couch 114. In some embodiments, the gantry 112 may include a tube, a detector, or other components. The tube may generate and/or emit one or more radiation beams directed toward a subject located on the couch 114. The detector may detect one or more radiation beams emitted from the tube of the gantry 112. In some embodiments, the gantry 112 may include a scanning region (also referred to as a detecting region or imaging region). The scanning region may be configured to accommodate a subject (e.g., a part of a patient) to be examined. The couch 114 may be configured to support a subject to be examined (e.g., a patient). In some embodiments, the couch 114 may be configured to transfer a subject (e.g., a patient) to a specified position (e.g., the scanning region in the gantry 112) to be examined. For example, when the couch 114 transfers a subject to the scanning region, the tube of the gantry 112 may emit a plurality of radiation beams directing toward the subject being examined, the detector of the gantry 112 may detect the traversed radiation beams and generate image data (e.g., projection data) related to the subject. In some embodiments, the scanner 110 may transmit the image data via, for example, the network 150 to the processing engine 120, the storage 130, and/or the terminal(s) 140. For example, the image data may be sent to the processing engine 120 for further processing, or may be stored in the storage 130.

In some embodiments, the couch 114 may include at least two supporting units and a board. The at least two supporting units may be configured to support the board. The at least two supporting units may be disposed at two sides of the scanning region of the gantry 112 or one of the at least two supporting units may be connected to the gantry 112. In some embodiments, the board may be configured to provide a supporting function, for example, supporting a subject being examined (e.g., a patient). In some embodiments, the board may traverse the scanning region of the gantry 112. At least one part of the board may be located in the scanning region of the gantry 112. The at least one part of the board located in the scanning region may include a first material. The first material may include a non-metal material, such as carbon fibers, resin, plastic, or the like, or a combination thereof. The rest part of the board that is located outside the scanning region of the gantry 112 may include a second material including metal, resin, plastic, fibers, etc. In some embodiments, the first material may be same as or different from the second material. For example, the first material and the second material may be both carbon fibers. As another example, the first material may include carbon fibers, and the second material may include a metal material. A thickness of the board may be configured to be smaller than a threshold (e.g., a pre-configured constant value) to decrease an attenuation of radiation rays (e.g., gamma rays) emitted from a subject being examined on the couch 114. The threshold may be configured to include 10 cm, 5 cm, 2 cm, etc.

In some embodiments, the couch 114 may further include a transmission belt and a drive component. The transmission belt may be configured to transfer a subject to the scanning region of the gantry 112. In some embodiments, the transmission belt may be configured to encompass the board, i.e., wrapping the upper surface and the bottom surface of the board. In some embodiments, the transmission belt may cover the upper surface of the board. For example, two ends of the transmission belt may be connected to two winding units, respectively. Through winding the transmission belt at one end while unwinding it at another end, the transmission belt is configured to move only on the upper surface of the board. The driving component may be configured to drive the transmission belt to move along the upper and bottom surface of the board. In some embodiments, the movement of the transmission belt may be controlled by a user via the terminal(s) 140. For example, a user may input an instruction by the terminal(s) 140 to start or stop the movement of the transmission belt. As another example, a user may control a movement speed of the transmission belt via the terminal(s) 140. In some embodiments, the driving component may further include a motor and at least two rotation wheels. The at least two rotation wheels may be connected with the at least two supporting units, respectively. In some embodiments, the at least two rotation wheels may be connected with two ends of the board, respectively. The motor may be connected to one of the at least two rotation wheels to drive the at least two rotation wheels to rotate. The motor may be configured to provide a power to the rotation of the at least two rotation wheels. The transmission belt may be configured to encompass the board and the at least two rotation wheels. The rotation of the at least two rotation wheels may drive the transmission belt to move.

The processing engine 120 may process data and/or information obtained from the scanner 110, the storage 130, and/or the terminal(s) 140. For example, the processing engine 120 may reconstruct an image based on projection data collected by the scanner 110. In some embodiments, the processing engine 120 may be a single server or a server group. The server group may be centralized or distributed. In some embodiments, the processing engine 120 may be local or remote. For example, the processing engine 120 may access information and/or data from the scanner 110, the storage 130, and/or the terminal(s) 140 via the network 150. As another example, the processing engine 120 may be directly connected to the scanner 110, the terminal(s) 140, and/or the storage 130 to access information and/or data. In some embodiments, the processing engine 120 may be implemented on a cloud platform. For example, the cloud platform may include a private cloud, a public cloud, a hybrid cloud, a community cloud, a distributed cloud, an inter-cloud, a multi-cloud, or the like, or a combination thereof.

The storage 130 may store data, instructions, and/or any other information. In some embodiments, the storage 130 may store data obtained from the processing engine 120, the terminal(s) 140, and/or the interaction device 150. In some embodiments, the storage 130 may store data and/or instructions that the processing engine 120 may execute or use to perform exemplary methods described in the present disclosure. In some embodiments, the storage 130 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 130 may be implemented on a cloud platform as described elsewhere in the disclosure.

In some embodiments, the storage 130 may be connected to the network 150 to communicate with one or more other components in the imaging system 100 (e.g., the processing engine 120, the terminal(s) 140, etc.). One or more components in the imaging system 100 may access the data or instructions stored in the storage 130 via the network 150. In some embodiments, the storage 130 may be part of the processing engine 120.

The terminal(s) 140 may be connected to and/or communicate with the scanner 110, the processing engine 120, and/or the storage 130. For example, the terminal(s) 140 may obtain a processed image from the processing engine 120. As another example, the terminal(s) 140 may obtain image data acquired via the scanner 110 and transmit the image data to the processing engine 130 to be processed. In some embodiments, the terminal(s) 140 may include a mobile device 141, a tablet computer 142, a laptop computer 143, or the like, or any combination thereof. For example, the mobile device 141 may include a mobile phone, a personal digital assistance (PDA), a gaming device, a navigation device, a point of sale (POS) device, a laptop, a tablet computer, a desktop, or the like, or any combination thereof. In some embodiments, the terminal(s) 140 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the processing engine 120 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the terminal(s) 140 may be part of the processing engine 120.

The network 150 may include any suitable network that can facilitate exchange of information and/or data for the imaging system 100. In some embodiments, one or more components of the imaging system 100 (e.g., the scanner 110, the processing engine 120, the storage 130, the terminal(s) 140, etc.) may communicate information and/or data with one or more other components of the imaging system 100 via the network 150. For example, the processing engine 120 may obtain image data from the scanner 110 via the network 150. As another example, the processing engine 120 may obtain user instruction(s) from the terminal(s) 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, witches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the imaging system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage 130 may be a data storage including cloud computing platforms, such as, public cloud, private cloud, community, and hybrid clouds, etc. However, those variations and modifications do not depart the scope of the present disclosure.

Figure 2:
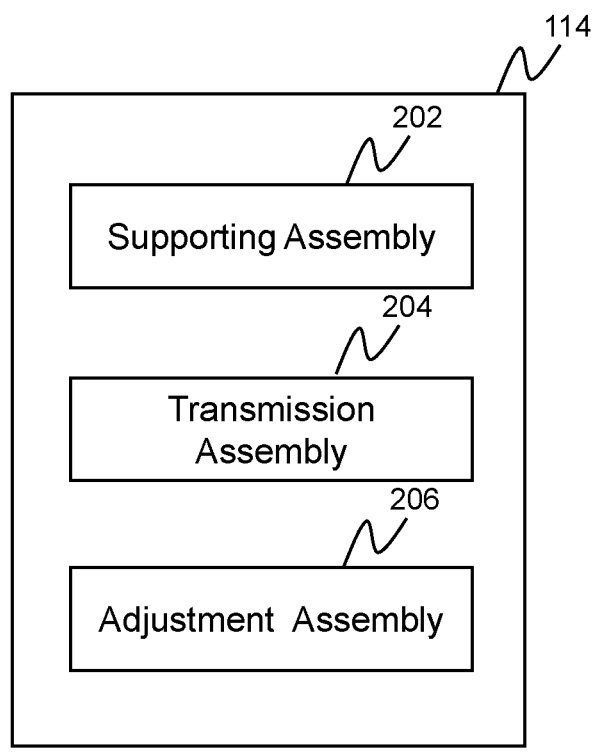
FIG. 2 is a block diagram illustrating an exemplary couch according to some embodiments of the present disclosure.

FIG. 2 is a block diagram illustrating an exemplary couch 114 according to some embodiments of the present disclosure. As shown in FIG. 2, the couch 114 may include a supporting assembly 202, a transmission assembly 204, and an adjustment assembly 206.

The supporting assembly 202 may be configured to provide a supporting function to the transmission assembly 204, the adjustment assembly 206, and/or other components of the couch 114. In some embodiments, the supporting assembly 202 may include a board and at least two supporting units (e.g., a first supporting unit and a second supporting unit). The at least two supporting units may be configured to support the board. In some embodiments, the at least two supporting units (e.g., the first supporting unit and the second supporting unit) may be spaced with a specified distance. The specified distance between the first supporting unit and the second supporting unit may be equal to or smaller than the length of the board. For example, the first supporting unit and the second supporting unit may be connected to two ends of the board respectively. As another example, the first supporting unit and the second supporting unit may be connected to any positions of the board between the two ends of the board.

In some embodiments, the at least two supporting units may be disposed at two sides of a scanning region of a scanner. In some embodiments, at least one of the at least two supporting units may be connected to a gantry of a scanner (e.g., the gantry 112 of the scanner 110). In some embodiments, at least one of the at least two supporting units may be disposed in a scanning region of a scanner.

The transmission assembly 204 may be configured to transfer a subject to, for example, a scanning region of a gantry of a scanner. In some embodiments, the transmission assembly 204 may include a first transmission belt and a first driving component. The first transmission belt may be configured to support and/or transfer the subject to, for example, a scanning region of a scanner. The first driving component may be configured to drive the first transmission belt. In some embodiments, the first driving component may include a first motor, a first rotation wheel and a second rotation wheel. The first motor may be connected to the first rotation wheel and/or the second rotation wheel. The first motor may drive the first rotation wheel and/or the second rotation wheel to rotate. In some embodiments, the transmission assembly 204 may be connected to and/or supported by at least part of the supporting assembly 202. For example, the first rotation wheel and the second rotation wheel may be connected to and/or supported by the two ends of the board respectively. As another example, the first rotation wheel and the second rotation wheel may be connected to and/or supported by the first supporting unit and the second supporting unit respectively. As a further example, one of the first rotation wheel and the second rotation wheel may be connected to the board of the supporting assembly 202, and another one of the first rotation wheel and the second rotation wheel may be connected to one of the first supporting unit and the second supporting unit of the supporting assembly 202. As still a further example, the first transmission belt may be configured to encompass the board of the supporting assembly 202, the first rotation wheel and the second rotation wheel. When the first motor drives the first rotation wheel and/or the second rotation wheel to rotate, the rotations of the first rotation wheel and/or the second rotation wheel may drive the first transmission belt to move, and transfer a subject located on the first transmission belt to a specified position (e.g., the scanning region of the scanner 110).

In some embodiments, the first rotation wheel and the second rotation wheel may be configured with a first gear and a second gear respectively. And thus, the first transmission belt may be configured with a plurality of teeth that can be coupled to the first gear and the second gear. The plurality of teeth may be configured on a surface of the first transmission belt in contact with the first gear and the second gear. In some embodiments, the board of the supporting assembly 202 may be configured with a groove. The groove may be configured to accommodate the plurality of teeth on the first transmission belt.

In some embodiments, the transmission assembly 204 may include a second transmission belt and a second driving component. The second transmission belt may be configured to support and/or transfer a subject to a specified position (e.g., the scanning region of the scanner 110). In some embodiments, the second driving component may include a second motor, a first winding unit, and a second winding unit. The first winding unit and the second winding unit may be connected to two ends of the second transmission belt respectively. In some embodiments, the second motor may be configured to provide power for the first winding unit and the second winding unit to rotate. The rotations of the first winding unit and the second winding unit may drive the second transmission belt to move. For example, the second transmission belt may be wound around the first winding unit and unwound from the second winding unit when the first winding unit and the second winding unit rotate in the same direction (e.g., a clockwise direction) synchronously to drive the transmission belt to move.

In some embodiments, the adjustment assembly 206 may include a first adjustment module. The first adjustment module may be configured to adjust a tension force of the first transmission belt or the second transmission belt of the transmission assembly 204. In some embodiments, the first adjustment module may be mounted on the board of the supporting assembly 202. In some embodiments, the first adjustment module may be connected to the transmission belt of the transmission assembly 204 (e.g., the first transmission belt or the second transmission belt). In some embodiments, the adjustment assembly 206 may further include a second adjustment module. The second adjustment module may be configured to adjust a space between the board of the supporting assembly 202 and the transmission belt of the transmission assembly 204 (e.g., the second transmission belt). In some embodiments, the second adjustment module may be mounted on at least one end of the board of the supporting assembly 202 close to the first winding unit or the second winding unit of the transmission assembly 204. In some embodiments, the second adjustment module may be connected to the transmission belt of the transmission assembly 204 (e.g., the second transmission belt). In some embodiments, the adjustment assembly 206 may include a third adjustment module. The third adjustment module may be configured to adjust a height of the board of the supporting assembly 202. In some embodiments, the third adjustment module may include at least two adjustment units (e.g., a first adjustment unit and a second adjustment unit). The at least two adjustment units may be configured to adjust heights of the at least two supporting units of the supporting assembly 202. The at least two adjustment units may be connected to the at least two supporting units of the supporting assembly 202 respectively. For example, the first adjustment unit may be connected to the first supporting unit and the second adjustment unit may be connected to the second supporting unit. In some embodiments, the at least two adjustment units may adjust heights of the at least two supporting units synchronously or asynchronously. For example, the first supporting unit and the second supporting unit may be adjusted synchronously by the first adjustment unit and the second adjustment unit such that the heights of the first supporting unit and the second supporting unit are equal. As another example, the first supporting unit and the second supporting unit may be adjusted by the first adjustment unit and the second adjustment unit asynchronously, and therefore, the heights of the first supporting unit and the second supporting unit may be different.

This description is intended to be illustrative, and not to limit the scope of the present disclosure. Many alternatives, modifications, and variations will be apparent to those skilled in the art. The features, structures, and other characteristics of the exemplary embodiments described herein may be combined in various ways to obtain additional and/or alternative exemplary embodiments. For example, the adjustment assembly 206 may be unnecessary and omitted. In some embodiments, the couch 114 may include at least two supporting assembly 202. For example, the couch 114 may include at least two boards, and each boards may be supported by at least two supporting units. However, those variations and modifications do not depart the scope of the present disclosure.

Figure 3:
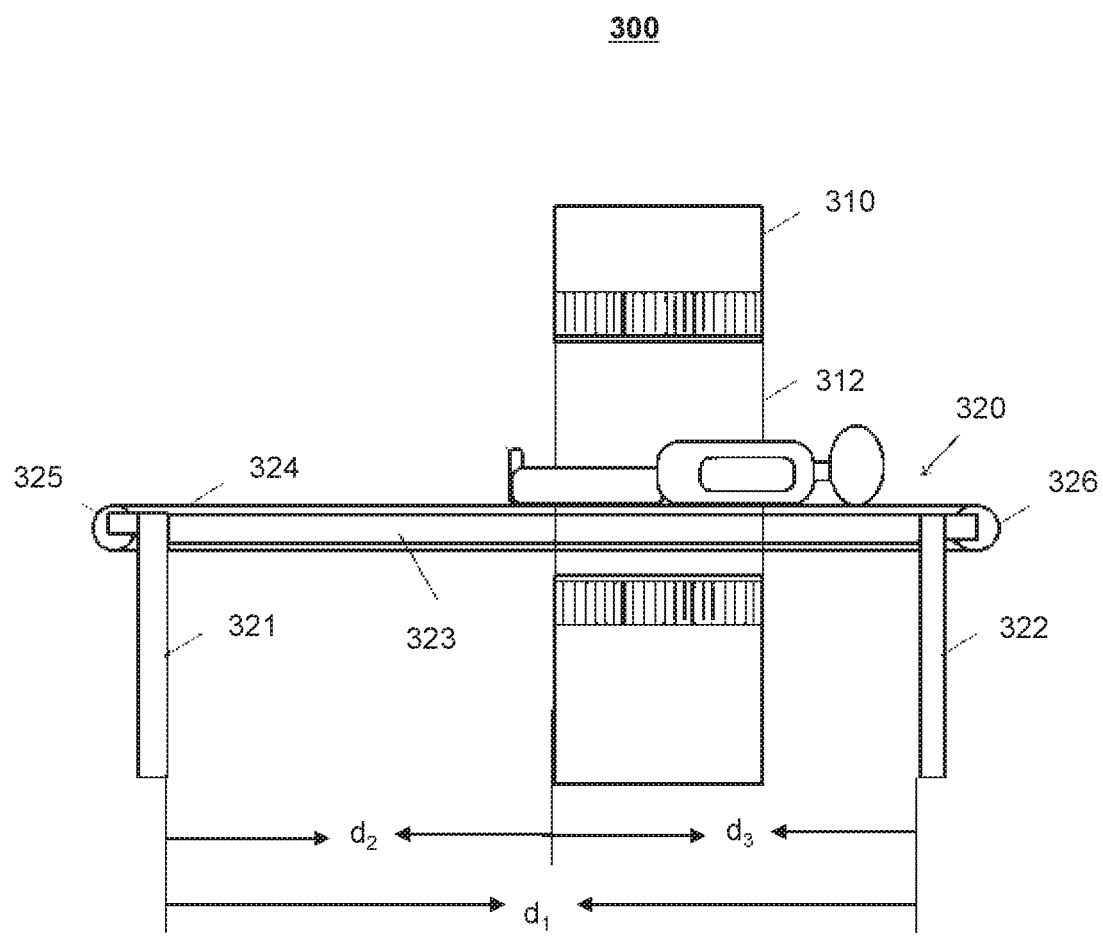
FIG. 3 is a schematic diagram illustrating an exemplary scanner from a side view according to some embodiments of the present disclosure.

FIG. 3 is a schematic diagram illustrating an exemplary scanner 300 from a side view according to some embodiments of the present disclosure. As shown in FIG. 3, the scanner 300 may include a gantry 310 and a couch 320. The gantry 310 may include a scanning region 312 configured to accommodate a subject being examined or treated as described in connection with FIG. 1. The couch 320 may include a first supporting unit 321, a second supporting unit 322, a board 323, a transmission belt 324, a first rotation wheel 325, and a second rotation wheel 326. The first supporting unit 321 and the second supporting unit 322 may be configured to perform a supporting function, for example, supporting the board 323, the first rotation wheel 325, and/or the second rotation wheel 326. In some embodiments, the first supporting unit 321 and the second supporting unit 322 may be connected to the board 323 spaced by a first distance $d_1$. The first distance may be smaller than or equal to the length of the board 323. For example, the first supporting unit 321 and the second supporting unit 322 may be connected to two ends of the board 323. The first supporting unit 321 and the second supporting unit 322 may be disposed at two sides of the gantry 310 or at the two sides of the scanning region 312 respectively. In some embodiments, the first supporting unit 321 and the gantry 310 or the scanning region 312 may be spaced by a second distance $d_2$. The second supporting unit 322 and the gantry 310 or the scanning region 312 may be spaced by a third distance $d_3$. In some embodiments, the first distance $d_1$ may be same with or different from the second distance $d_2$. For example, the first distance $d_1$ may be greater than the second distance $d_2$. As another example, the first distance $d_1$ may be smaller than the second distance $d_2$.

In some embodiments, the couch 320 may further include an adjustment component (not shown) associated with the first supporting unit 321 and the second supporting unit 322. The adjustment component may be configured to adjust a height of the board 323. For example, the adjustment component may include a first lifting apparatus and a second lifting apparatus. The first lifting apparatus and the second lifting apparatus may be connected to the first supporting unit 321 and the second supporting unit 322 respectively. The first lifting apparatus and the second lifting apparatus may be configured to adjust the lengths of the first supporting unit 321 and the second supporting unit 322 respectively. In some embodiments, the adjustment component may further include a driving member configured to drive, for example, the first lifting apparatus and/or the second lifting apparatus to lift. The driving member may include a hydraulic cylinder, a motor, or the like, or a combination thereof.

The transmission belt 324 may be configured to support and/or transfer a subject (e.g., a patient) to the scanning region 312. The transmission belt 324 may be configured to encompass the first rotation wheel 325, the board 323, and the second rotation wheel 326. In some embodiments, the couch 320 may further include a motor (not shown in FIG. 3). The motor may be connected with at least one of the first rotation wheel 325 and the second rotation wheel 326. The motor may drive the at least one of the first rotation wheel 325 and the second rotation wheel 326 to rotate. The rotations of the first rotation wheel 325 and the second rotation wheel 326 may drive the transmission belt 324 to perform a movement.

This description is intended to be illustrative, and not to limit the scope of the present disclosure. Many alternatives, modifications, and variations will be apparent to those skilled in the art. The features, structures, and other characteristics of the exemplary embodiments described herein may be combined in various ways to obtain additional and/or alternative exemplary embodiments. For example, the couch 300 may further include at least one supporting unit. The at least one supporting unit may be connected to a position of the board 323 between the first supporting unit 321 and the second supporting unit 322. However, those variations and modifications do not depart the scope of the present disclosure.

Figure 4A:
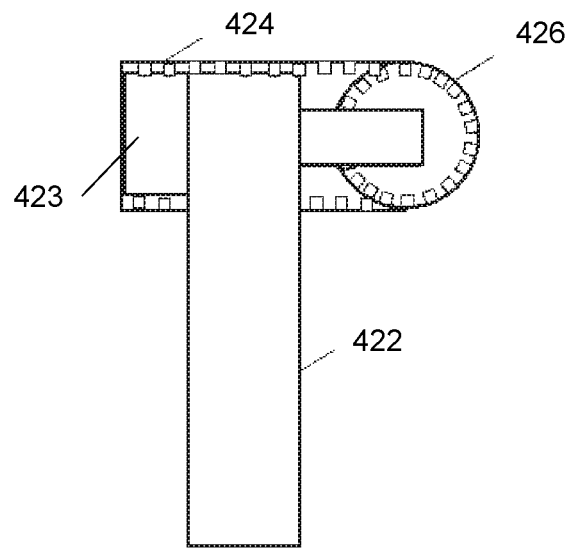
FIGS. 4A and 4B are schematic diagrams illustrating two perspective views of at least one part of an exemplary couch according to some embodiments of the present disclosure.
Figure 4B:
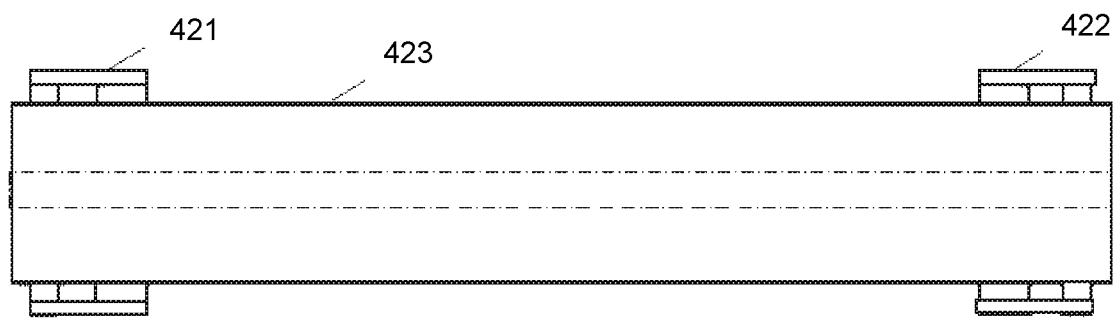

FIGS. 4A and 4B are schematic diagrams illustrating two perspective views of at least one part of an exemplary couch 400 according to some embodiments of the present disclosure. A difference between the couch 400 and the couch 320 as illustrated in FIG. 3 is that at least one of the first rotation wheel (not shown in FIG. 4A) and the second rotation wheel 426 of the couch 400 may be configured with gears, and a transmission belt 424 may be configured with a plurality of teeth disposed on the lower surface of the transmission belt 424. The plurality of teeth of the transmission belt 424 may be coupled with the gears of the first rotation wheel and the second rotation wheel 426. A board 423 may be configured with a groove indicated by the two dotted lines as shown in FIG. 4B. The groove may be configured to accommodate the plurality of teeth of the transmission belt 424.

Figure 5:
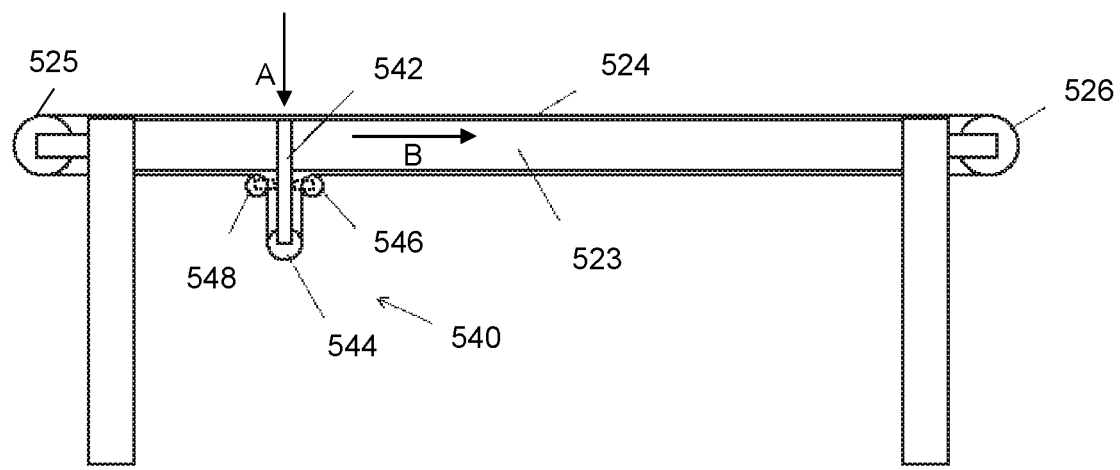
FIG. 5 is a schematic diagram illustrating an exemplary couch according to some embodiments of the present disclosure.

FIG. 5 is a schematic diagram illustrating an exemplary couch 500 according to some embodiments of the present disclosure. A difference between the couch 500 and the couch 320 as illustrated in FIG. 3 is that the couch 500 may further include an adjustment component 540 configured to adjust a tension force of a transmission belt 524. As shown in FIG. 5, the adjustment component 540 may include a third supporting unit 542, a third rotation wheel 544, a fourth rotation wheel 546, and a fifth rotation wheel 548.

The third supporting unit 542 may be connected to and/or support the third rotation wheel 544, the fourth rotation wheel 546, and/or the fifth rotation wheel 548. In some embodiments, the third supporting unit 542 may be mounted on a board 523. In some embodiments, the third supporting unit 542 may be mounted on the ground directly. In some embodiments, the third supporting unit 542 may be mounted on a base detectably located on the ground. In some embodiments, the third supporting unit 542 may be configured to extend along a direction perpendicular to the surface of the transmission belt 524 or the board 523 (e.g., the direction indicated by arrow A) such that the length of the third supporting unit 542 may be increased or decreased. When the length of the third supporting unit 542 increases, the tension of the transmission belt 524 increases accordingly. When the length of the third supporting unit 542 decreases, the tension force of the transmission belt 524 decreases accordingly. In some embodiments, the third supporting unit 542 may be configured to move along the long axis direction of the transmission belt 524 or the board 523 (e.g., the direction indicated by arrow B).

The third rotation wheel 544 may be connected to an end of the third supporting unit 542 opposite to the end of the third supporting unit 542 connected to the board 523. The transmission belt 524 may be configured to encompass the board 523, a first rotation wheel 525, a second rotation 526, and the third rotation wheel 544. In some embodiments, the tension force of the transmission belt 524 may relate to a distance from the third rotation wheel 544 to one surface of the board 523. The distance from the third rotation wheel 544 to one surface of the board 523 may relate to the length of the third supporting unit 542. The greater the distance between the third rotation wheel 544 and the surface of the board 523 is, the greater the tension force of the transmission belt 524 may receive. In some embodiments, the third rotation wheel 544 may be a driving wheel. The third rotation wheel 544 may be connected to and driven by a motor (not shown) to rotate. Rotations of the third rotation wheel 544 may drive rotations of the first rotation wheel 525 and the second rotation wheel 526. Then, the transmission belt 524 may move along the rotations of the first rotation wheel 525, the second rotation wheel 526, and the third rotation wheel 544.

The fourth rotation wheel 546 and the fifth rotation wheel 548 may be configured to keep the transmission belt 524 parallel to the board 523 when the transmission belt 524 encompasses the third rotation wheel 544. The fourth rotation wheel 546 and the fifth rotation wheel 548 may be disposed at two sides of the third supporting unit 542. In some embodiments, the fourth rotation wheel 546 and/or the fifth rotation wheel 548 may be connected to the board 523 and/or the third supporting unit 542 via, for example, rods indicated by dot lines as shown in FIG. 5

This description is intended to be illustrative, and not to limit the scope of the present disclosure. Many alternatives, modifications, and variations will be apparent to those skilled in the art. The features, structures, and other characteristics of the exemplary embodiments described herein may be combined in various ways to obtain additional and/or alternative exemplary embodiments. For example, the adjustment component 540 may further include a fourth supporting unit and a fifth supporting unit connected to the fourth rotation wheel 546 and the fifth rotation wheel 548 respectively. In some embodiments, the fourth supporting unit and the fifth supporting unit may be mounted on the ground directly or a base mounted on the ground detectably. However, those variations and modifications do not depart the scope of the present disclosure.

Figure 6:
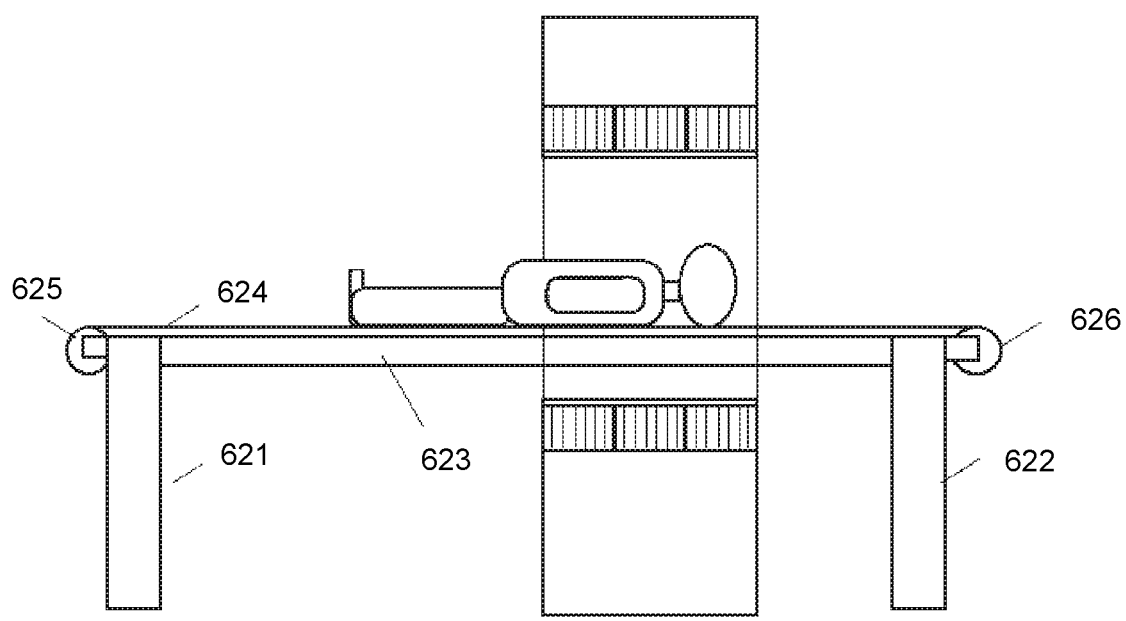
FIG. 6 is a schematic diagram illustrating an exemplary scanner according to some embodiments of the present disclosure.

FIG. 6 is a schematic diagram illustrating an exemplary scanner 600 according to some embodiments of the present disclosure. A difference between the scanner 600 and the scanner 300 illustrated in FIG. 3 is that the first rotation wheel 325 and the second rotation wheel 326 of the couch 320 as illustrated in FIG. 3 may be replaced by a first winding unit 625 and a second winding unit 626 respectively. The first winding unit 625 and the second winding unit 626 may be configured to wind a transmission belt 624 around the first winding unit 625 or the second winding unit 626 such that the transmission belt 624 may perform a movement. In some embodiments, the first winding unit 625 and the second winding unit 626 may be mounted on two ends of a board 623 respectively. In some embodiments, the first winding unit 625 and the second winding unit 626 may be connected to a first supporting unit 621 and a second supporting unit 622 respectively. Two ends of the transmission belt 624 may be connected to the first winding unit 625 and the second winding 626 respectively. The first winding unit 625 and the second winding 626 may be driven by a motor (not shown) to rotate. The rotations of the first winding unit 625 and the second winding unit 626 may drive the transmission belt 624 to perform a movement. For example, when the first winding unit 625 and the second winding unit 626 both rotate clockwise, the transmission belt 624 may be wound around the second winding unit 626, and the transmission belt 624 may move toward the second winding unit 626. When the first winding unit 625 and the second winding unit 626 both rotate anticlockwise, the transmission belt 624 may be wound around the first winding unit 625, and the transmission belt 624 may move toward the first winding unit 625.

This description is intended to be illustrative, and not to limit the scope of the present disclosure. Many alternatives, modifications, and variations will be apparent to those skilled in the art. The features, structures, and other characteristics of the exemplary embodiments described herein may be combined in various ways to obtain additional and/or alternative exemplary embodiments. For example, the couch 620 may further include a third supporting unit and a fourth supporting unit configured to support the first winding unit 625 and the winding unit 626 respectively. The third supporting unit and the fourth supporting unit may be mounted on the ground directly or a base mounted on the ground detectably. However, those variations and modifications do not depart the scope of the present disclosure.

Figure 7:
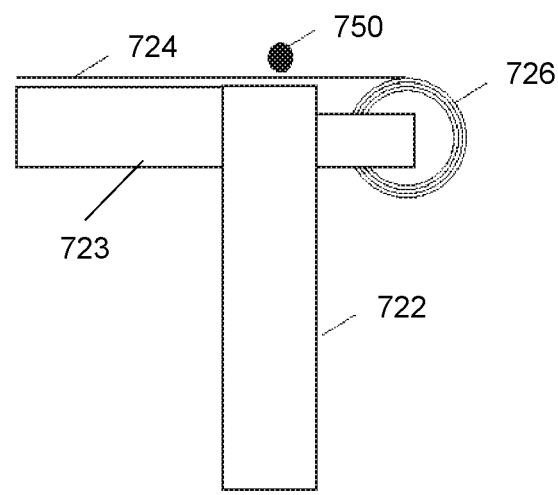
FIG. 7 is a schematic diagram illustrating a part of an exemplary couch according to some embodiments of the present disclosure.

FIG. 7 is a schematic diagram illustrating a part of an exemplary couch 700 according to some embodiments of the present disclosure. A difference between the couch 700 and the couch 620 as illustrated in FIG. 6 is that the couch 700 may further include an adjustment component 750 configured to adjust a space between a transmission belt 724 and a board 723. In some embodiments, the adjustment component 750 may include one or more spacing cylinders. In some embodiments, the one or more spacing cylinders may be mounted on the board 723 close to the second winding unit 726 (or a first winding unit not shown in FIG. 7). When the second winding unit 726 (or the first winding unit) winds multiple layers of the transmission belts 724, the outermost layer of the transmission belt 724 wound around the second winding unit 726 may be further away from the upper surface of the board 723. The space between the board 723 and the transmission belt 724 at a position close to the second winding unit 726 (or the first winding unit) may be greater than the space at a position between the board 723 and the transmission belt 723 far away the second winding unit 726 (or the first winding unit), such as the middle position of the board 723. The one or more spacing cylinders mounted close to the second winding unit 726 (or the first winding unit) may be configured to keep the transmission belt 724 close to and/or parallel to the board 723 approximatively.

Figure 8:
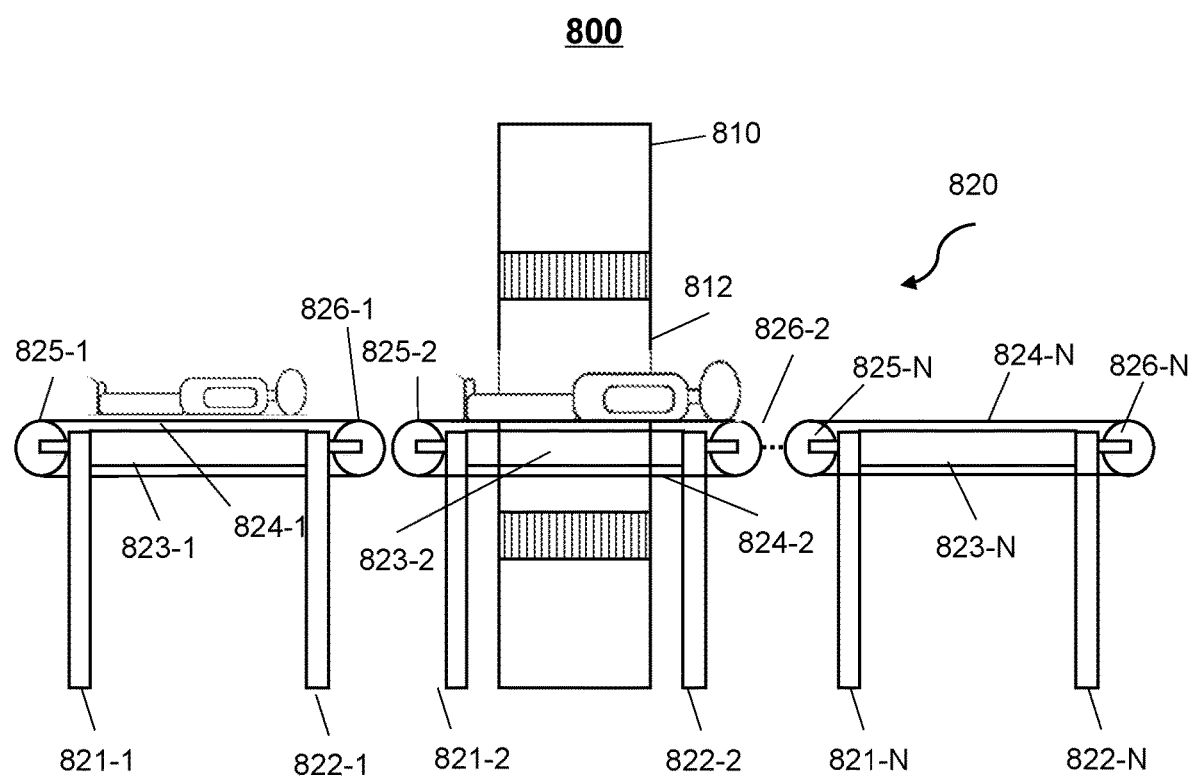
FIG. 8 is a schematic diagram illustrating an exemplary scanner 800 according to some embodiments of the present disclosure.

FIG. 8 is a schematic diagram illustrating an exemplary scanner 800 according to some embodiments of the present disclosure. As shown in FIG. 8, the scanner 800 may include a gantry 810 and a couch 820. The gantry 810 may include a scanning region 812 configured to accommodate a subject, or at least a part of the subject (e.g., a patient). The couch 820 may be configured to support and/or transfer a subject to a specified position (e.g., the scanning region 812). The couch 820 may include multiple boards (e.g., a first board 823-1, a second board 823-2, . . . , an Nth board 823-N). Each of the multiple boards may be supported by at least two supporting units. For example, the first board 823-1 may be supported by a first supporting unit 821-1 and a second supporting unit 822-1. As another example, the Nth board 823-N may be supported by a first supporting unit 821-N and a second supporting unit 822-N. In some embodiments, the couch 820 may further include multiple transmission belts (e.g., a first transmission belt 824-1, a second transmission belt 824-2, . . . , an Nth transmission belt 824-N). The multiple transmission belts may be configured to transfer a subject to a specified position (e.g., the scanning region 812). In some embodiments, the couch 820 may further include multiple pairs of rotation wheels (e.g., a first rotation wheel 825-1 and a second rotation wheel 826-1, a first rotation wheel 825-2, and a second rotation wheel 826-2, . . . , a first rotation wheel 825-N, and a second rotation wheel 826-N.). One of the multiple boards (e.g., the first board 823-1) may be configured with one transmission belt (e.g., the first transmission belt 824-1) and one pair of rotation wheels (e.g., the first rotation wheel 825-1 and the second rotation wheel 826-1). Each of the multiple transmission belts may be configured to encompass one board and one pair of rotation wheels. For example, the first transmission belt 824-1 may be configured to encompass the first board 823-1, the first rotation wheel 825-1, and the second rotation wheel 826-1. As another example, an Nth transmission belt 824-N may be configured to encompass the Nth board 823-N, the first rotation wheel 825-N and the second rotation wheel 826-N. In some embodiments, the couch 820 may further include at least one driven unit (e.g., a motor) configured to drive the multiple first rotation wheels and/or the multiple second rotation wheels to rotate synchronously or asynchronously. For example, a pair of rotation wheels may be configured with a motor. One single motor may drive just one single pair of rotation wheels to rotate. The rotations of the pair of rotation wheels may drive the transmission belt connected to the pair of rotation wheels to move. The multiple transmission belts may be configured with multiple motors. The multiple transmission belts may be controlled to move synchronously or asynchronously by controlling the multiple motors via the terminal(s) 140. In some embodiments, multiple subjects to be examined may be located on the couch 820. For example, one of the multiple subjects may be located on one of the multiple transmission belts. The multiple subjects may be transferred by the multiple transmission belts synchronously or asynchronously by controlling the multiple motors via the terminal(s) 140. For example, a first subject may be located on the first transmission belt 824-1. The second subject may be located on the second transmission belt 824-2. The second subject may be transferred to the scanning region 812 by the second transmission belt 824-2, and the first subject may be not moved on the transmission belt 824-1. As another example, the first subject and the second subject may be moved by the first transmission belt 824-1 and the second transmission belt 824-2 synchronously, such that the first subject may be transferred to the second transmission belt 824-2 and the second subject may be transferred to next transmission belt (e.g., a third transmission belt 824-3 not shown).

In some embodiments, the couch 820 may further include an adjustment component (not shown). The adjustment component may be configured to adjust heights of the multiple boards (e.g., the first board 823-1, the second boards 823-2, . . . , the Nth boars 823-N). In some embodiments, the adjustment component may include multiple adjustment modules (e.g., a first adjustment module, a second adjustment module, . . . , an Nth adjustment module) corresponding to the multiple boards. Each of the multiple adjustment modules may be configured to adjust a height of one of the multiple boards (e.g., the first board 823-1, the second boards 823-2, . . . , the Nth boars 823-N). In some embodiments, the multiple adjustment modules may adjust heights of the multiple boards synchronously or asynchronously. For example, the first board 823-1 and the second board 823-2 may be adjusted by the first adjustment module and the second adjustment module synchronously such that the heights of the first board 823-1 and the second board 823-2 is equal. As another example, the first board 823-1 and the second board 823-2 may be adjusted by the first adjustment module and the second adjustment module asynchronously such that the height of the first board 823-1 may be lower or higher than that of the second board 823-2.

This description is intended to be illustrative, and not to limit the scope of the present disclosure. Many alternatives, modifications, and variations will be apparent to those skilled in the art. The features, structures, and other characteristics of the exemplary embodiments described herein may be combined in various ways to obtain additional and/or alternative exemplary embodiments. For example, the multiple first rotation wheels and the multiple second rotation wheels may be replaced by multiple first winding units and multiple second winding units. As another example, the couch 820 may include just two boards. In some embodiments, the multiple transmission belts may be integrated into one single transmission belt. The single transmission belt may be configured to encompass the multiple boards, the multiple first rotation wheels (e.g., the first rotation wheel 825-1, the first rotation wheel 825-2, ..., the first rotation wheel 825-N.), and the multiple second rotation wheels (e.g., the second rotation wheel 826-1, the second rotation wheel 826-2, ..., the second rotation wheel 826-N.). However, those variations and modifications do not depart the scope of the present disclosure.

Figure 9:
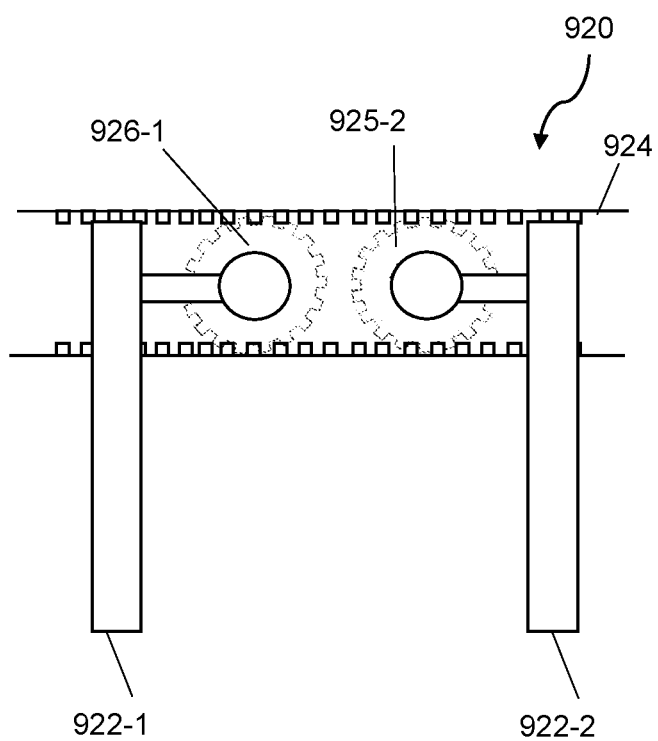
FIG. 9 is schematic diagrams illustrating at least one part of an exemplary couch according to some embodiments of the present disclosure

FIG. 9 is schematic diagrams illustrating at least one part of an exemplary couch 920 according to some embodiments of the present disclosure. A difference between the couch 920 and the couch 820 as illustrated in FIG. 8 is that multiple first rotation wheels (e.g., a first rotation wheel 926-1) and multiple second rotation wheels (e.g., a second rotation wheel 925-1) of the couch 920 may be configured with gears, and a transmission belt 924 may be configured with a plurality of teeth disposed on the lower surface of the transmission belt 924. The plurality of teeth of the transmission belt 924 may be coupled with the gears of the multiple first rotation wheels and the multiple second rotation wheels (e.g., the first rotation wheel 926-1 and the second rotation wheel 925-2). The rotations of the multiple first rotation wheels and the multiple second rotation wheels may drive the transmission belt 924 to perform a movement. In some embodiments, the transmission belt 924 may be configured to encompass the multiple first rotation wheels and the multiple second rotation wheels.

This description is intended to be illustrative, and not to limit the scope of the present disclosure. Many alternatives, modifications, and variations will be apparent to those skilled in the art. The features, structures, and other characteristics of the exemplary embodiments described herein may be combined in various ways to obtain additional and/or alternative exemplary embodiments. For example, at least one of the multiple boars may be configured with a first winding unit and a second winding unit replacing the first rotation wheel and the second rotation wheel. However, those variations and modifications do not depart the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and describe.

What is claimed is:

1. A device for transferring a subject in a medical procedure, the device comprising:
    a transmission assembly configured to transfer the subject to a scanning region of a medical device, the transmission assembly including at least one transmission belt and at least one first adjustment component, the at least one first adjustment component being configured to adjust a tension force of the at least one transmission belt, wherein the at least one first adjustment component includes at least one first supporting unit, and the tension force of the at least one transmission belt is adjusted by adjusting a length of the at least one first supporting unit; and
    a supporting assembly supporting the transmission assembly, the supporting assembly including at least one board and at least two supporting units supporting the at least one board, wherein the at least two supporting units are disposed at two sides of the scanning region of the medical device, and the at least two supporting units at least include a second supporting unit and a third supporting unit.

2. The device of claim 1, wherein the transmission assembly further includes:
    at least one driving component configured to drive the at least one transmission belt.

3. The device of claim 2, wherein the at least one driving component further includes:
    a first rotation wheel; and
    a second rotation wheel,
    wherein the at least one transmission belt is configured to encompass the first rotation wheel, the second rotation wheel and the at least one board, and the first rotation wheel and the second rotation wheel are configured to rotate to drive a rotation of the at least one transmission belt.

4. The device of claim 3, wherein each of the first rotation wheel and the second rotation wheel is configured with a gear, respectively.

5. The device of claim 4, wherein the at least one transmission belt is configured with a plurality of teeth being coupled with the gears, and the at least one board is configured with a groove to accommodate the plurality of teeth.

6. The device of claim 2, wherein the at least one driving component further includes:
    a first winding component; and
    a second winding component,
    wherein the first winding component and the second winding component are connected to two ends of the at least one transmission belt, respectively.

7. The device of claim 2, wherein the transmission assembly further includes at least one second adjustment component configured to adjust a space between the at least one board and the at least one transmission belt, the at least one second adjustment component being connected to the supporting assembly.

8. The device of claim 1, wherein one of the at least two supporting units is connected to a gantry of the medical device.

9. The device of claim 3, wherein the at least one first adjustment component includes at least one third rotation wheel, the at least one transmission belt encompassing the at least one third rotation wheel.

10. The device of claim 7, wherein the supporting assembly further includes at least one third adjustment component connected to at least one of the at least two supporting units, the at least one third adjustment component being configured to adjust a height of the at least one board.

11. The device of claim 10, wherein the at least one third adjustment component includes a first adjustment unit and a second adjustment unit, the first adjustment unit and the second adjustment are connected to the at least two supporting units, respectively.

12. The device of claim 1, wherein the at least one first supporting unit is configured to move along an axis direction of the at least one transmission belt or the at least one board.

13. A system for performing a medical procedure, comprising:
   a medical device, including a scanning region being configured to accommodate a subject; and
   a device configured to transfer the subject to the scanning region, including
      a transmission assembly configured to transfer the subject to the scanning region of the medical device, the transmission assembly including at least one transmission belt and at least one first adjustment component, the at least one first adjustment component being configured to adjust a tension force of the at least one transmission belt, wherein the at least one first adjustment component includes at least one first supporting unit, and the tension force of the at least one transmission belt is adjusted by adjusting a length of the at least one first supporting unit; and
      a supporting assembly supporting the transmission assembly, the supporting assembly including at least one board and at least two supporting units supporting the at least one board, wherein the at least two supporting units are disposed at two sides of the scanning region of the medical device, and the at least two supporting units at least include a second supporting unit and a third supporting unit.

14. The system of claim 13, wherein one of the at least two supporting units is connected to a gantry of the medical device.

15. The system of claim 13, wherein the transmission assembly includes:
   at least one driving component configured to drive the at least one transmission belt.

16. The system of claim 15, wherein the at least one driving component further includes:
   a first rotation wheel; and
   a second rotation wheel,
   wherein the at least one transmission belt is configured to encompass the first rotation wheel, the second rotation wheel and the at least one board, and the first rotation wheel and the second rotation wheel are configured to rotate to drive a rotation of the at least one transmission belt.

17. The system of claim 15, wherein the at least one driving component further includes:
   a first winding component; and
   a second winding component,
   wherein the first winding component and the second winding component are connected to two ends of the at least one transmission belt, respectively.

18. The system of claim 13, wherein the transmission assembly further includes at least one second adjustment component configured to adjust a space between the at least one board and the at least one transmission belt, the at least one second adjustment component being connected to the supporting assembly.

19. The system of claim 18, wherein the supporting assembly further includes at least one third adjustment component connected to at least one of the at least two supporting units, the at least one third adjustment component being configured to adjust a height of the at least one board.

* * * * *